(12) United States Patent
Nishimura et al.

(10) Patent No.: US 7,057,077 B2
(45) Date of Patent: Jun. 6, 2006

(54) METHOD FOR PRODUCING 2-(ALKYL) CYCLOALKENONE

(75) Inventors: Hirotsugu Nishimura, Wakayama (JP); Koji Mine, Wakayama (JP)

(73) Assignee: Kao Corporation, Tokyo (JP)

( * ) Notice: Subject to any disclaimer, the term of this patent is extended or adjusted under 35 U.S.C. 154(b) by 50 days.

(21) Appl. No.: 10/732,360

(22) Filed: Dec. 11, 2003

(65) Prior Publication Data

US 2004/0171886 A1 Sep. 2, 2004

(30) Foreign Application Priority Data

Dec. 26, 2002 (JP) .............................. 2002-378006

(51) Int. Cl.
*C07C 45/51* (2006.01)
*C07C 69/74* (2006.01)
*C07D 305/00* (2006.01)
*C07D 309/00* (2006.01)

(52) U.S. Cl. ............... 568/341; 568/361; 560/122; 549/263; 549/273

(58) Field of Classification Search ........... 568/341, 568/361; 560/122; 549/263, 273
See application file for complete search history.

(56) References Cited

U.S. PATENT DOCUMENTS

| 4,260,830 A | 4/1981 | Wilson et al. ............... 562/485 |
| 6,500,990 B1 * | 12/2002 | Asada et al. ................ 568/341 |
| 6,833,481 B1 * | 12/2004 | Yamamoto et al. ......... 568/341 |

FOREIGN PATENT DOCUMENTS

| EP | 0 033 604 | 8/1981 |
| EP | 1 134 210 | 9/2001 |
| JP | 56-147740 | 11/1981 |
| JP | 2001-328965 | 11/2001 |

OTHER PUBLICATIONS

Kazmierczak et al. Synthesis of the Branched Nine-Carbon Unit of the Type A Streptogramins and Other Antibiotics. Journal of Organic Chemistry, 1989, vol. 54, p. 3988-3992.*
Derwent Publications, JP 9 104681, Apr. 22, 1997.
Derwent Publications, JP 51 023240, Feb 24, 1976.
Derwent Publications, JP 5 092934, Apr. 16, 1993.
Derwent Publications, JP 55 120533, Sep. 17, 1980.

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

A method for producing 2-(alkyl)cycloalkenone and a method for producing alkyl(3-oxo-2-alkylcycloalkyl) acetate and 5-alkyl-5-alkanolide which are useful as flavoring materials and physiologically active substances using the same are provided. A method for producing Compound (2) including the steps of: dehydrating Compound (1) using an acid catalyst until the conversion ratio of dehydration reaction reaches 20 to 90% based on Compound (1), thereby obtaining a mixture containing Compound (1) and Compound (3); and isomerizing Compound (3) while dehydrating the remaining Compound (1), and a method for producing Compound (5) or (6) using obtained Compound (2).

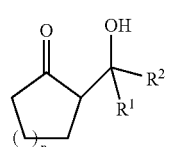

(1)

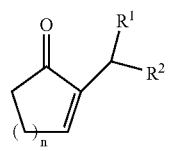

(2)

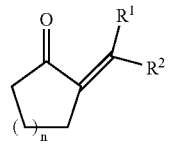

(3)

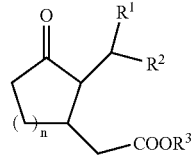

(5)

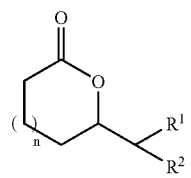

(6)

(wherein n represents 1 or 2, $R^1$ and $R^2$ each represent H, $C_{1-8}$ alkyl groups and the like and $R^3$ represents $C_{1-3}$ alkyl groups).

18 Claims, No Drawings

METHOD FOR PRODUCING 2- (ALKYL) CYCLOALKENONE

TECHNICAL FIELD

The present invention relates to a method for producing 2-(alkyl)cycloalkenone which is an intermediate for synthesis of methyl dihydrojasmonate, δ-lactone and the like which are useful as flavoring materials, and to a method for producing alkyl(3-oxo-2-alkylcycloalkyl)acetate and 5-alkyl-5-alkanolide using the same compound.

BACKGROUND ART

Conventionally, as a method for producing 2-(alkyl)cycloalkenone from 2-(1-hydroxyalkyl)cycloalkanone, for example, JP-A 56-147740 discloses a method in which after dehydrating an aldol condensed compound with oxalic acid, isomerization reaction is allowed using hydrogen bromide and hydrochloric acid, or a method in which dehydration reaction and subsequent isomerization reaction are simultaneously conducted with the use of hydrogen bromide and hydrogen chloride. When using strong acids such as hydrogen bromide and hydrogen chloride, the reaction proceeds to isomerization reaction as well as dehydration reaction. However, since 2-(1-hydroxyalkyl)cycloalkanone which is a raw material and 2-(alkyl)cycloalkenone which is a product polymerize and decompose, decrease in yield is inevitable.

Additionally, in comparison with the reaction wherein the above dehydration reaction and isomerization reaction simultaneously take place, a two-step method in which isomerization reaction takes place after dehydration reaction using a weak acid such as oxalic acid sometimes causes deterioration in yield due to polymerization and decomposition of 2-(alkyl)cycloalkenone when the dehydration reaction is forced to proceed to a high conversion ratio.

On the other hand, JP-A 2001-328965 discloses a method of simultaneously conducting dehydration reaction and isomerization reaction by acting a catalyst containing amine and hydrogen halide on 2-(1-hydroxyalkyl)cycloalkanone. However, the temperature that allows efficient isomerization reaction is in the range of 80 to 200° C. in industrial production.

SUMMARY OF THE INVENTION

The present invention relates to a method for producing 2-(alkyl)cycloalkenone with efficiency and with high yield in mild conditions, and a method for producing alkyl(3-oxo-2-alkylcycloalkyl)acetate and 5-alkyl-5-alkanolide which are useful as flavoring materials or physiologically active substances using the same.

The present invention provides a method for producing 2-(alkyl)cycloalkenone (hereinafter referred to as Compound (2)) represented by the formula (2) as shown below, by using as a raw material 2-(1-hydroxyalkyl)cycloalkanone (hereinafter referred to as Compound (1)) represented by the following formula (1):

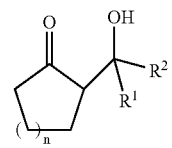

(wherein n represents an integer of 1 or 2, $R^1$ and $R^2$ each represent a hydrogen atom or a straight or branched-chain alkyl group having 1 to 8 carbon(s), or $R^1$ and $R^2$ may form together with adjacent carbon atoms a cyclopentane ring or a cyclohexane ring), the method including a dehydration step as described below followed by an isomerization step;

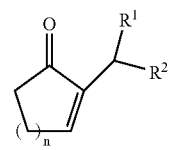

(wherein n, $R^1$ and $R^2$ represent the meanings as defined above).

Dehydration step: using an acid catalyst, the reaction is allowed to proceed until a conversion ratio of hydration reaction based on Compound (1) reaches to 20 to 90%, to obtain a mixture containing Compound (1) and 2-(alkylidene)cycloalkanone (hereinafter referred to as Compound (3)) represented by the formula (3):

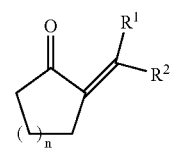

(wherein n, $R^1$ and $R^2$ represent the meanings as defined above).

Isomerization step: Compound (3) is allowed to isomerize while allowing dehydration reaction of remaining Compound (1).

In addition, the present invention provides a method for producing alkyl(3-oxo-2-alkylcycloalkyl)acetate (hereinafter referred to as Compound (5)) represented by the formula (5) as shown below, the method including the steps of allowing Compound (2) obtained in the above method to react with malonic acid diester (hereinafter referred to as Compound (4)) represented by the formula (4):

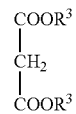

(wherein R³ represents a straight or branched-chain alkyl group having 1 to 3 carbon(s), and two R³s may be the same or different);

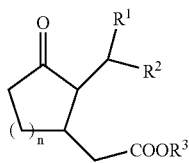

(5)

(wherein n, R¹, R² and R³ represent the same meanings as defined above).

Also the present invention provides a method for producing 5-alkyl-5-alkanolide (hereinafter referred to as Compound (6)) represented by the formula (6):

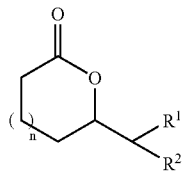

(6)

(wherein n, R¹ and R² represent the same meanings as defined above), the method including the steps of subjecting hydrogen-reducing Compound (2) obtained by the above production method and subjecting to Bayer-Villiger oxidation.

DETAILED EXPLANATION OF THE INVENTION

In the state of arts a method of efficiently obtaining 2-(alkyl)cycloalkenone in milder conditions is desired.

According to the method of the present invention, it is possible to produce 2-(alkyl)cycloalkenone with high yield and high productivity. Furthermore, by using the obtained 2-(alkyl)cycloalkenone, it is possible to produce alkyl(3-oxo-2-alkylcycloalkyl)acetate and 5-alkyl-5-alkanolide which are useful as flavoring materials and physiologically active substances with high yield and high purity.

[Production Method of Compound (2)]

In Compound (1) used as a raw material of the present invention, examples of the alkyl group constituting 1-hydroxyalkyl group include a methyl group, ethyl group, propyl group, isopropyl group, butyl group, isobutyl group, amyl group, isoamyl group, hexyl group, heptyl group and the like.

This Compound (1) can be produced in a generally known manner, and for example, it can be obtained by reacting a cycloalkanone having 5 or 6 carbons with an aldehyde or ketone represented by the following formula (7):

(7)

(wherein R¹ and R² represent the same meanings as defined above).

In the present invention, Compound (1) obtained in the manner as described above may be directly used without undergoing distillation, however, it may be used after purified by distillation in such a case that activity of acid catalyst decreases.

In the dehydration step of the present invention, as the catalyst for the dehydration reaction, acid catalysts preferably having pKa (acid dissociation exponent in aqueous solution) of not less than 0, more preferably in the range of 0.5 to 7 are used. Furthermore, the catalyst may be a catalyst of homogenous system or a solid catalyst. Among others, phosphoric acid, condensed phosphoric acid, oxalic acid and sulfuric acid are preferred, and phosphoric acid, condensed phosphoric acid and sulfuric acid are more preferred.

From the viewpoint of the reactivity and economical viewpoint, the used amount of the catalyst is preferably from 0.01 to 20% by weight, more preferably 0.1 to 10% by weight, much more preferably from 0.5 to 10% by weight, relative to Compound (1) which is a raw material.

In the dehydration step of the present invention, if the conversion ratio of dehydration reaction is too small, the heating load associated with the dehydration reaction conducted in the isomerization step increases, making it difficult to keep the reaction temperature that allows efficient isomerization reaction (80 to 200° C.), while on the other hand, if the conversion ratio of dehydration reaction is too high, Compound (1) which is a raw material and Compound (3) which is a product of dehydration reaction will polymerize and decompose, to lead deterioration in yield. For this reason, the conversion ratio of dehydration reaction is preferably from 20 to 90%, more preferably from 40 to 90%, and still preferably from 50 to 80%. Herein the conversion ratio of dehydration reaction is a value defined by the following expression (I).

$$\text{Conversion ration of dehydration reaction [\%]} = 100 - \frac{\text{amount of Compound (1) (mole) in reaction}}{\text{amount of charged compound (1) (mole)}} \times 100 \qquad (I)$$

The reaction temperature of the dehydration step is preferably from 70 to 150° C., and more preferably from 90 to 120° C. from the viewpoint of finishing the reaction in a short time and preventing Compound (3) from polymerizing and decomposing to avoid deterioration in yield. As for the reaction pressure, the reaction can proceed even at atmospheric pressure, however, in order to achieve efficient reaction by efficiently distilling off the generated water but not the raw material and the reaction product from the system, the reaction is preferably conducted in reduced pressures ranging from 20 to 80 kPa.

In the isomerization step of the present invention, when the acid catalyst remains in the reaction product after completion of the dehydration reaction, it is preferred to neutralize it because it may possibly decrease the activity of the catalyst for isomerization reaction. The isomerization reaction may be conducted using a known method, and for example, as disclosed in Japanese Unexamined Patent Publication JP-A 2001-328965, it is preferred to simultaneously conduct the dehydration reaction and the isomerization reaction by acting a catalyst containing an amine and a hydrogen halide on a mixture containing Compound (1) and Compound (3), because this provides Compound (2) with high yield.

As the amine used herein, aromatic amines or heteroaromatic amines such as aniline, diphenylamine, pyridine, picoline, quinoline, polyvinylpyridine and the like are preferred, with pyridine, picoline and quinoline being particularly preferred. As the hydrogen halide, hydrogen chloride, hydrogen bromide or hydrogen iodide is recited, and hydrogen chloride or hydrogen bromide is particularly preferred. The molar ratio of amine and hydrogen halide is preferably amine/hydrogen halide (molar ratio)=1.1/1 to 5/1.

The reaction is preferably conducted in an alcohol solvent or in absence of a solvent. Examples of the alcohol solvent include methanol, ethanol, 1-propanol, 2-propanol, butanol, pentanol, hexanol, 2-ethylhexanol, cyclohexanol, ethyleneglycol, 1,8-octandiol, glycerin, polyethyleneglycol and the like, and lower alcohols having 1 to 8 carbon(s) are particularly preferred. The reaction temperature is preferably from 80 to 200° C., and particularly from 100 to 180° C.

[Production Method of Compound (5)]

Using compound (2) obtained in the above production method as a raw material, Compound (5) which is useful as a flavoring material or physiologically active substance can be obtained in the manner as disclosed in JP-A 56-147740, for example.

More specifically, Compound (2) and Compound (4) are allowed to react in the presence of a basic catalyst, to obtain the compound represented by the following formula (8) (hereinafter referred to as Compound (8)):

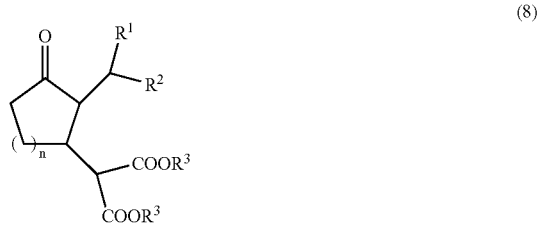

(wherein n, $R^1$, $R^2$ and $R^3$ have the same meanings as defined above).

Compound (4) is allowed to react in an amount of preferably 1 to 5 times by mole, more preferably 1.2 to 2 times by mole, relative to Compound (2).

As the basic catalyst, alkaline metals such as sodium and potassium, alkaline metal alkoxides such as sodium alkoxide and potassium alkoxide and the like can be exemplified. The use amount of the catalyst is preferably from 0.02 to 0.2 times by mole, relative to Compound (2). As the solvent, polar solvents such as alcohols are preferred. The reaction temperature is preferably from −10 to 30° C., and more preferably from 0 to 20° C.

Next, by reacting Compound (8), thus obtained, with water, it is possible to produce Compound (5). It is preferred to let the water react in such a manner that it is dropped into the reaction system in an amount of 1 to 3 times by mole, relative to Compound (8). The reaction temperature is preferably in the range of 150 to 220° C.

[Production Method of Compound (6)]

Using Compound (2) obtained in the above production method as a raw material, Compound (6) which is useful as a flavoring material or physiologically active substance can be obtained in a generally known manner.

For example, Compound (2) is hydrogen-reduced in the presence of a catalyst such as Pd/C, to afford the compound represented by the following formula (9) (hereinafter referred to as Compound (9)):

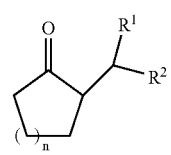

(wherein n, $R^1$ and $R^2$ have the same meanings as defined above).

Compound (9), thus obtained, is subjected to Baeyer-Villiger oxidation using peracetic acid or the like as an oxidant as described, for example, in JP-A 9-104681, to afford Compound (6).

EXAMPLES

In the following examples, quantification of the product was carried out by an internal standard method using gas chromatography (as an internal standard, carbitol was used for dehydration reaction and undecane was used for isomerization reaction). Dehydration reaction yield is defined by the expression (II), and isomerization reaction yield is defined by the expression (III).

Dehydration reaction yield [%]=(Total amount (mole) of Compound (1) and Compound (3) in reaction/Total amount (mole) of charged Compound (1) and Compound (3))×100   (II)

Isomerization reaction yield [%]=(Amount (mole) of Compound (2) in reaction/Total amount (mole) of charged Compound (1) and Compound (3))×100   (III)

Production Example 1

A 6 m³-reaction tank equipped with a feeding tank was charged with 2241 kg (26.6 kmol) of cylopentanone, 1007 kg of water and 11 kg of 48% NaOH, cooled to 15° C. under stirring, and then continuously added with 985 kg (11.4 kmol) of valeraldehyde over 5 hours at the same temperature. After completion of the dropping, the reaction mixture was stirred at the same temperature for an hour. After completion of the reaction, the reaction mixture was neutralized, and excess cylopentanone was collected by distillation. Then the organic phase was analyzed to find that 1868 kg of the final product contained 1658 kg of 2-(1-hydroxypentyl)-cyclopentanone and 40 kg of 2-pentylidenecyclopentanone.

Example 1

To a 6 m³-reaction vessel equipped with a simple distillation line (pipe-line) containing 1893 kg of a liquid organic matter containing 1677 kg (9.8 kmol) of 2-(1-hydroxypentyl)-cyclopentanone and 52 kg (0.3 kmol) of 2-pentylidenecyclopentanone obtained in the same manner as Production example 1, 17 kg of 105% phosphoric acid catalyst was added, and heated and mixed so as to reach 100° C. and 40 kPa. After allowing to react for 1.5 hours, the reaction mixture was cooled to room temperature, and the reaction finish product was analyzed to find that it contained 464.5 kg (2.7 kmol) of unreacted 2-(1-hydroxypentyl)-cyclopentanone and 1058.2 kg (7.0 kmol) of 2-pentylidenecyclopentanone which is a dehydrated product. The conversion ratio of dehydration reaction was 72.3%, and the dehydration reaction yield was 95.0%.

A part of the reaction finish product was neutralized with 48% NaOH, and 300.2 g of the organic phase was drawn out. A 1000 mL-tetra-neck flask equipped with a dehydration tube was charged with a mixture of 300.0 g of 2-ethylhexanol, 17.4 g of 3-picoline and 17.7 g of 35% HCl, heated to 140° C., and added dropwise with the above organic phase over 2 hours. After completion of the dropping, the reaction mixture was heated and stirred for 5 hours at the same temperature. After completion of the reaction, the mixture was cooled to room temperature and the organic phase was analyzed to find that the reaction finish product contained 198.5 g of 2-pentyl-2-cyclopentenone. The isomerization reaction yield was 78.6%. General yield obtained by dehydration reaction yield times isomerization reaction yield was 74.7%.

Example 2

To a 2L-reaction vessel equipped with a single distillation column containing 1000 g of a liquid organic matter containing 860.2 g (5.05 mol) of 2-(1-hydroxypentyl)-cyclopentanone and 32.0 g (0.21 mol) of 2-pentylidenecyclopentanone obtained in the same manner as Production example 1, 8.7 g of 105% phosphoric acid was added, and heated and mixed so as to reach 100° C. and 40 kPa. After allowing to react for 0.5 hour, the reaction mixture was cooled to room temperature and the reaction finish product was analyzed to find that it contained 390.6 g (2.29 mol) of unreacted 2-(1-hydroxypentyl)-cyclopentanone and 426.3 g (2.80 mol) of 2-pentylidenecyclopentanone which is a dehydrated product. The conversion ratio of dehydration reaction was 54.6%, and the dehydration reaction yield was 96.8%.

A part of the reaction finish product is neutralized with 48% NaOH, and 100 g of the organic phase is drawn out. A 1000 mL-tetra-neck flask equipped with a dehydration tube was poured with a mixture of 100 g of 2-ethylhexanol, 5.3 g of 3-picoline and 5.4 g of 35% HCl, heated to 140° C., and add dropwise with the above organic phase over 2 hours. After completion of the dropping, the reaction mixture is heated under stirring for 4 hours at the same temperature. After completion of the reaction, the mixture is cooled to room temperature and the organic phase is analyzed to find that the reaction finish product contained 63.5 g of 2-pentyl-2-cyclopentenone. The isomerization reaction yield will be 80%. General yield obtained by dehydration reaction yield times isomerization reaction yield will be 77%.

Comparative Example 1

To a similar vessel as described in Example 1 containing 1791 kg of a liquid organic matter containing 1361 kg (8.0 kmol) of 2-(1-hydroxypentyl)-cyclopentanone and 65 kg (0.4 kmol) of 2-pentylidenecyclopentanone obtained in the same manner as Production example 1, 14 kg of 105% phosphoric acid catalyst was added, and heated and mixed so as to reach 100° C. and 40 kPa. After allowing to react for 4 hours, the reaction mixture was cooled to room temperature, and the reaction finish product was analyzed to find that it contained 19 kg (0.1 kmol) of unreacted 2-(1-hydroxypentyl)-cyclopentanone and 1128 kg (7.4 kmol) of 2-pentylidenecyclopentanone which is a dehydrated product. The conversion ratio of dehydration reaction was 98.6%, and the dehydration reaction yield was 89.4%.

A part of the reaction finish product was neutralized with 48% NaOH, and 1551 kg of the organic phase was drawn out. A 6 m$^3$-reaction vessel equipped with a single distillation column was charged with a mixture of 1551 kg of 2-ethylhexanol, 76 kg of 3-picoline and 84 kg of 35% HCl, heated to 140° C., and added dropwise with the above organic phase over 1.8 hours. After completion of the dropping, the reaction mixture was heated and stirred for 5 hours at the same temperature. After completion of the reaction, the mixture was cooled to room temperature and the organic phase was analyzed to find that the reaction finish product contained 811 kg of 2-pentyl-2-cyclopentenone. The isomerization reaction yield was 71.9%. General yield obtained by dehydration reaction yield times isomerization reaction yield was 64.2%.

Example 3

The reaction finish product synthesized in the similar manner as Example 1 was rectificated, to obtain 190 g (1.2 mol) of 2-pentyl-2-cyclopentene. Then to a mixture obtained by dissolving 236 g (1.8 mol) of dimethyl malonate in 76 g of anhydrous methanol under nitrogen atmosphere, cooling to 0° C., and adding 12.9 g (0.072 mmol) of sodium methoxide (30% in methanol), 190 g (1.2 mol) of 2-pentyl-2-cyclopentene obtained above was added dropwise at 0° C. over 2 hours. After completion of the dropping, the resultant mixture was stirred at the same temperature for 3 hours. Unreacted dimethyl malonate was distilled off under reduced pressures, to afford 320 g of a Michael addition product.

A reaction apparatus equipped with a distillation outlet tube was added with the Michael addition product obtained above and heated to 215° C., and then water was added dropwise at a rate of 6.4 g/h (2%/h). While distilling off the generating carbon dioxide and methanol, the dropping reaction was conducted for 4 hours at 215° C. After completion of the reaction, 245 g of methyl 3-oxo-2-pentylcyclopenthyl acetate was obtained in 251 g of the crude product.

Methyl 3-oxo-2-pentylcyclopenthyl acetate obtained by rectificating the crude product had fruity and jasmine-like flavor, and was excellent as a flavoring material.

What is claimed is:

1. A method for producing 2-(alkyl)cycloalkenone of formula (2) comprising dehydrating and isomerizing 2-(1-hydroxyalkyl)cycloalkanone of formula (1):

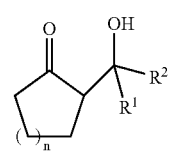

(1)

wherein n represents an integer of 1 or 2, $R^1$ and $R^2$ each represent a hydrogen atom or a straight or branched-chain alkyl group having 1 to 8 carbon(s), or $R^1$ and $R^2$ may form together with adjacent carbon atoms a cyclopentane ring or a cyclohexane ring,

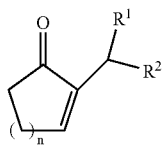

(2)

wherein n, $R^1$ and $R^2$ represent the meanings as defined above, wherein dehydration is conducted using an acid catalyst, the reaction proceeding until a conversion ratio of dehydration reaction based on Compound (1) reaches to 20 to 90%, to obtain a mixture containing Compound (1) and 2-(alkylidene) cycloalkanone of formula (3):

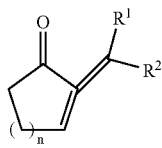

(3)

wherein n, $R^1$ and $R^2$ represent the meanings as defined above; and Compound (3) is isomerized while dehydrating remaining Compound (1).

2. The method according to claim 1, wherein a pKa of the acid catalyst used in the dehydration step is not less than 0.

3. The method according to claim 1 or 2, wherein the acid catalyst used in the dehydration step is at least one selected from phosphoric acid, condensed phosphoric acid and sulfuric acid.

4. A method for producing alkyl(3-oxo-2-alkylcycloalkyl)acetate, the method comprising the steps of:

reacting 2-(alkyl)cycloalkenone obtained by the method according to claim 1 or 2 with malonic acid diester represented by the formula (4):

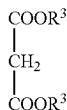

(4)

COOR$^3$
|
CH$_2$
|
COOR$^3$ wherein $R^3$ represents a straight or branched-chain alkyl group having 1 to 3 carbon(s), and two $R^3$s may be the same or different, and reacting with water, to thereby produce alkyl(3-oxo-2-alkylcycloalkyl) acetate represented by the formula (5):

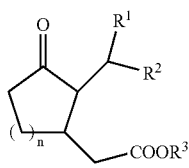

(5)

wherein n represents an integer of 1 or 2, $R^1$ and $R^2$ each represent a hydrogen atom or a straight or branched-chain alkyl group having 1 to 8 carbon(s), or $R^1$ and $R^2$ may form together with adjacent carbon atoms a cyclopentane ring or a cyclohexane ring.

5. A method for producing 5-alkyl-alkanolide represented by the formula (6):

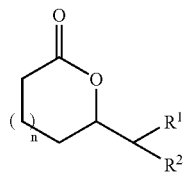

(6)

wherein n represents an integer of 1 or 2, $R^1$ and $R^2$ each represent a hydrogen atom or a straight or branched-chain alkyl group having 1 to 8 carbon(s), or $R^1$ and $R^2$ may form together with adjacent carbon atoms a cyclopentane ring or a cyclohexane ring, the method comprising the steps of:

hydrogen-reducing 2-(alkyl)cycloalkenone obtained in the method according to claim 1 or 2, and subjecting the resultant compound to Bayer-Villiger oxidation.

6. The method according to claim 1, wherein a pKa of the acid catalyst used in the dehydration step is in the range of 0.5 to 7.

7. The method of claim 1, wherein said acid catalyst is used in an amount of from 0.01 to 20 wt. %.

8. The method of claim 1, wherein said conversion ratio is from 40 to 90%.

9. The method of claim 1, wherein said conversion ratio is from 50 to 80%.

10. The method of claim 1, wherein said dehydration is conducted at a temperature of from 70 to 150° C.

11. The method of claim 1, wherein said acid catalyst is neutralized after completion of said dehydration reaction.

12. The method of claim 1, wherein Compound (3) is isomerized while dehydrating remaining Compound (1) by the action of catalyst comprising an amine and a hydrogen halide.

13. The method of claim 12, wherein said amine is at least one selected from the group consisting of aromatic amines and heteroaromatic amines.

14. The method of claim 12 wherein said amine is at least one selected from the group consisting of aniline, diphenylamine, pyridine, picoline, quinoline, polyvinylpyridine.

15. The method of claim 12, wherein said hydrogen halide is at least one selected from the group consisting of hydrogen chloride, hydrogen bromide and hydrogen iodide.

16. The method of claim 12, wherein a molar ratio of amine and hydrogen halide is 1.1/1 to 5/1.

17. The method of claim 1, wherein said isomerizing is conducted in at least one solvent selected from the group consisting of methanol, ethanol, 1-propanol, 2-propanol, butanol, pentanol, hexanol, 2-ethylhexanol, cyclohexanol, ethyleneglycol, 1,8-octandiol, glycerin and polyethyleneglycol.

18. The method of claim 1, wherein said isomerizing is conducted at a reaction temperature of 80 to 200° C.

* * * * *

UNITED STATES PATENT AND TRADEMARK OFFICE
CERTIFICATE OF CORRECTION

PATENT NO.        : 7,057,077 B2
APPLICATION NO. : 10/732360
DATED             : June 6, 2006
INVENTOR(S)       : Hirotsugu Nishimura et al.

It is certified that error appears in the above-identified patent and that said Letters Patent is hereby corrected as shown below:

In the Claims:

Claim 1, Column 9, lines 17-25, replace structure of formula (3)

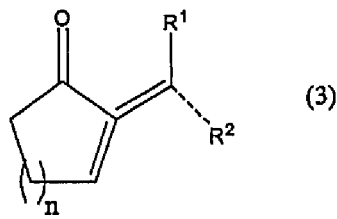

with

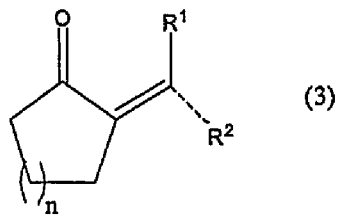

Signed and Sealed this

Sixth Day of November, 2007

JON W. DUDAS
*Director of the United States Patent and Trademark Office*